(12) United States Patent
Wang et al.

(10) Patent No.: US 6,934,353 B2
(45) Date of Patent: Aug. 23, 2005

(54) METHODS, APPARATUS, AND COMPUTER READABLE MEDIUMS FOR PERFORMING PERFUSION STUDIES

(75) Inventors: Ge Wang, Iowa City, IA (US); Jiang Hsieh, Brookfield, WI (US); Yuchuan Wei, Iowa City, IA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 40 days.

(21) Appl. No.: 10/676,215

(22) Filed: Oct. 1, 2003

(65) Prior Publication Data

US 2005/0074084 A1 Apr. 7, 2005

(51) Int. Cl.⁷ .................................................. A61B 6/03
(52) U.S. Cl. .............................. 378/8; 378/15; 378/901
(58) Field of Search ........................... 378/4, 8, 15, 901

(56) References Cited

U.S. PATENT DOCUMENTS

| | | | |
|---|---|---|---|
| 4,059,010 A | 11/1977 | Sachs | |
| 4,610,021 A | 9/1986 | Peschmann et al. | |
| 5,081,660 A | 1/1992 | Fujisaki | |
| 5,848,117 A | 12/1998 | Urchuk et al. | |
| 6,041,097 A | 3/2000 | Roos et al. | |
| 6,307,909 B1 | 10/2001 | Flohr et al. | |
| 6,381,487 B1 | 4/2002 | Flohr et al. | |
| 6,589,502 B1 | 7/2003 | Coniglione et al. | |
| 2002/0173715 A1 * | 11/2002 | Kruger et al. | 600/410 |

* cited by examiner

Primary Examiner—David V Bruce
(74) Attorney, Agent, or Firm—Carl B. Horton, Esq.; Armstrong Teasdale LLP (57) ABSTRACT

A method for conducting a perfusion study includes performing an initial full scan of an area of interest in an object, and performing at least one subsequent partial scan of the area of interest to detect motion of a contrast agent.

23 Claims, 8 Drawing Sheets

Image at time
t-2Δt, $f_{t-2\Delta t}(x,y)$

Image at time
t-Δt, $f_{t-\Delta t}(x,y)$

"Initial guess" image
at time t, $f_t(x,y)$

METHODS, APPARATUS, AND COMPUTER READABLE MEDIUMS FOR PERFORMING PERFUSION STUDIES

BACKGROUND OF THE INVENTION

This invention relates generally to Computed Tomography (CT) imaging systems, and more particularly to projection interpolation algorithms and image prediction algorithms for low dose perfusion technology.

CT perfusion is a recent advancement in clinical applications. In such a scan, the organ-of-interest is repeatedly scanned in a cine mode (table remains stationary during the scan) while the contrast medium is injected into the patient and propagated in the blood circulation. By monitoring the contrast uptake of the different part of the organ, the mean transit time (MTT), cerebral blood flow (CBF), cerebral blood volume (CBV), and other parameters can be calculated. These parameters are used to differentiate viable versus non-viable tissues. In the current protocol, the patient is continuously scanned at one-second intervals for 30 to 40 second(s).

It is desirable to reduce the amount of dose to the patient. One known way is to reduce the milliamperage of the x-ray tube current directly. Because a low milliampereage results in higher noise in the projection data, one will get a sequence of noisy images. At least some basic algorithms exist to reduce noise either in projection or image spaces. However, once the noise is introduced into the collected projection data, it is difficult to remove it completely.

BRIEF DESCRIPTION OF THE INVENTION

In one aspect, a method for conducting a perfusion study is provided. The method includes performing an initial full scan of an area of interest in an object, and performing at least one subsequent partial scan of the area of interest to detect motion of a contrast agent.

In another aspect, a Computed Tomography (CT) System includes a radiation source, a radiation detector, and a computer coupled to the radiation source and the radiation detector. The computer is configured to perform an initial full scan of an area of interest in an object, and perform at least one subsequent partial scan of the area of interest to detect motion of a contrast agent.

In yet another aspect, a computer readable medium encoded with a program is provided. The program is configured to instruct a computer to perform an initial full scan of an area of interest in an object, and perform at least one subsequent partial scan of the area of interest to detect motion of a contrast agent.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
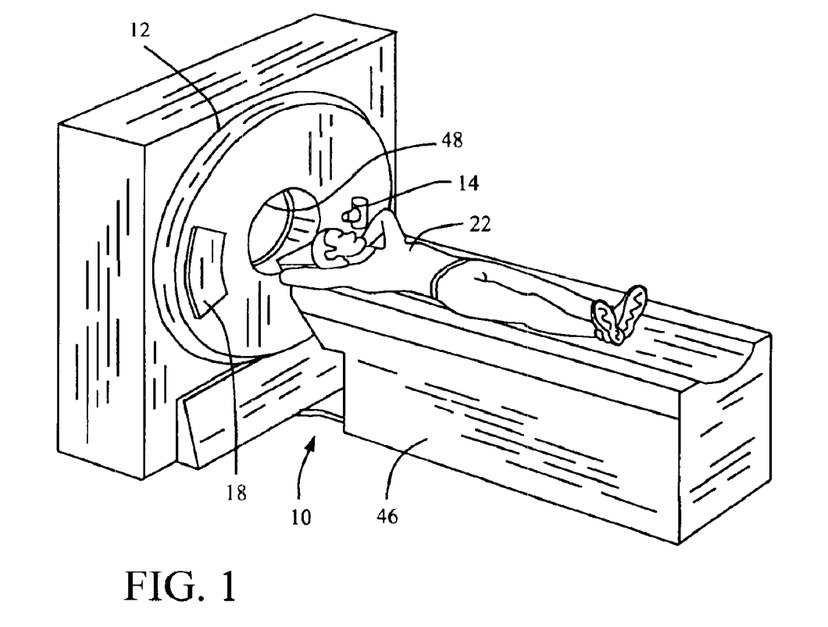
FIG. 1 is a pictorial view of a CT imaging system.
Figure 2:
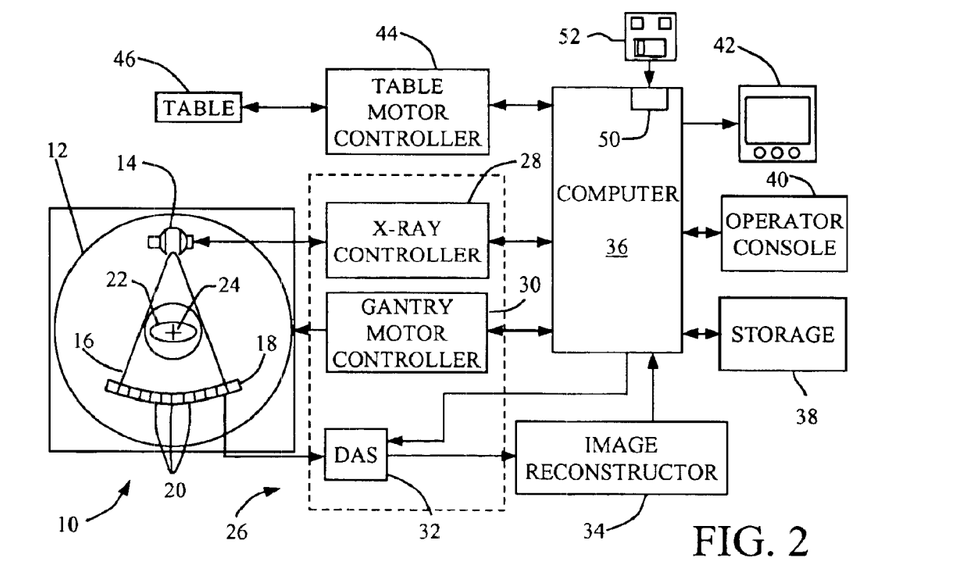
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT.

Herein described are methods and apparatus to avoid the high noise data in the low dose case, using scanning protocols and associated algorithms. The herein described methods include Partial Scan Protocols (PSP), an associated Projection Interpolation Algorithm (PIA), and an Image Prediction Algorithm (IPA).

One characteristic of the herein described protocols is to maintain the high tube current and reduce the number of views in an existing scanning protocol, because when the milliamperage is high to tube 14, the data noise is low.

Figure 3:
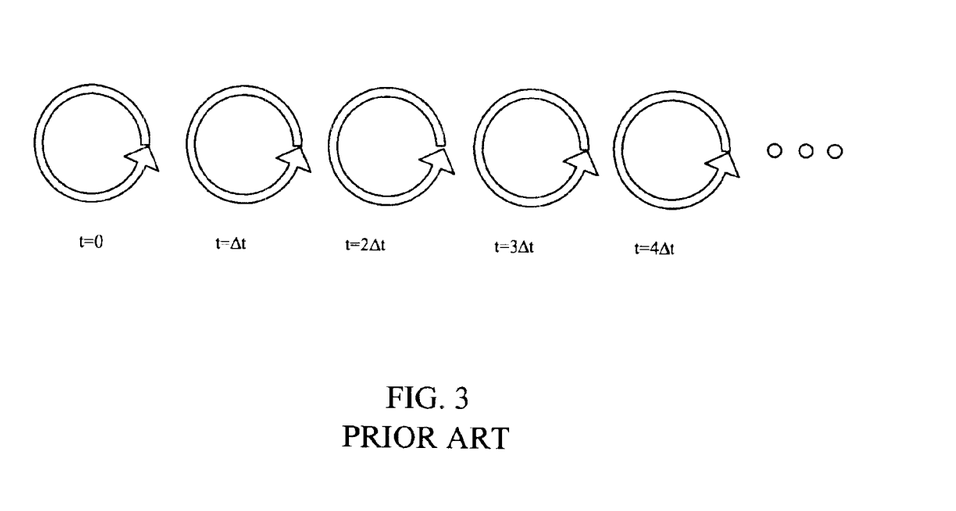
FIG. 3 (prior art) shows existing scanning protocol.

As shown in FIG. 3, using a known protocol, a complete (360 degree) projection dataset is acquired every $\Delta t$ time interval. Every image is independently reconstructed from its complete dataset to provide a sequence of images for perfusion analysis. For the purpose of low dose, the x-ray tube current is typically set to a relatively low milliamperage. Thus, projection data collected according to the protocol illustrated in FIG. 3 has a low signal-to-noise ratio and much effort is spent on noise reduction.

Figures 4, 5:
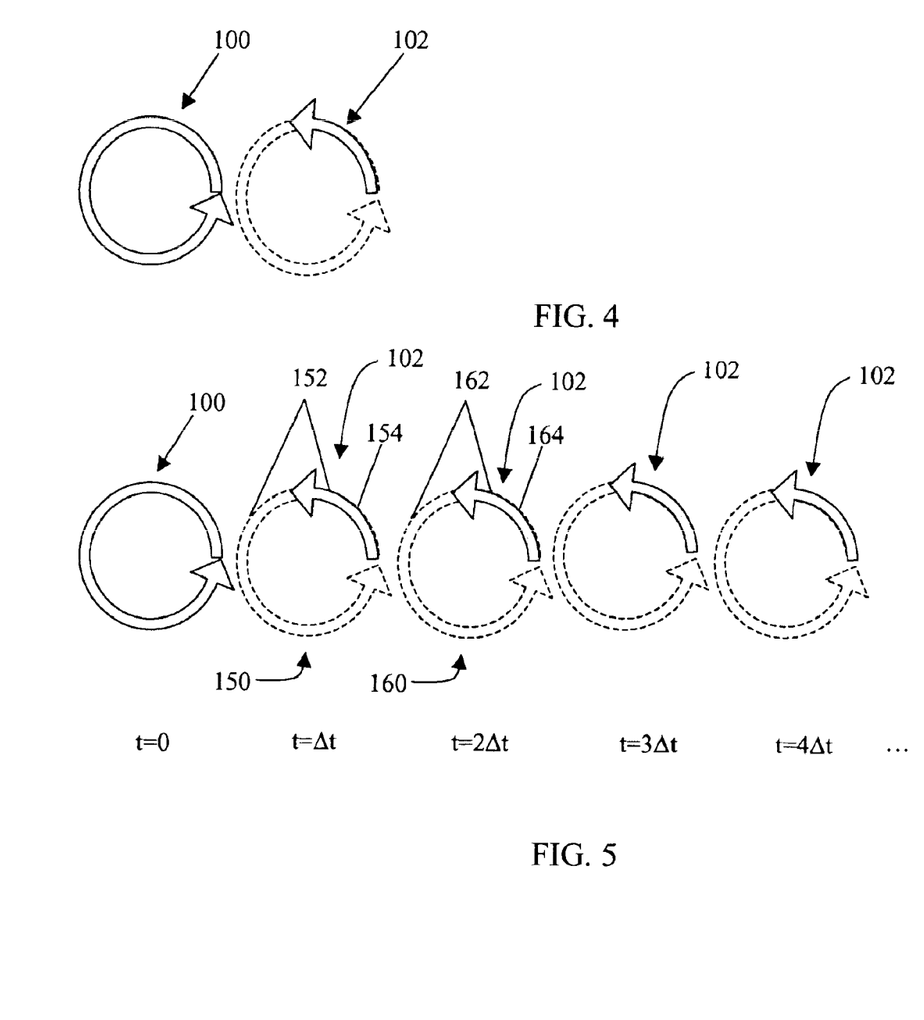
FIG. 4 illustrates a partial scan following a full scan.
FIG. 5 illustrates a fixed partial scan.

FIG. 4 illustrates an initial full scan 100 of an area of interest in an object, followed by a partial scan 102 of the area of interest to detect motion of a contrast agent. As used herein, the term "full scan" refers to both full scans in which data is collected for all views of a 360° scan and half scans in which data is collected for all views of a scan of 180° plus a fan angle. Additionally, as used herein, the term partial scan refers to all scans in which data is collected for views representing less than 180° plus a fan angle.

FIG. 5 illustrates partial scans 102 of one embodiment of FIG. 4, including performing a first full rotation 150 including n sub-rotations 152, where no scanning is performed for all sub-rotations except an ith sub-rotation 154 in which a scan is performed. This is followed by performing a second full rotation 160 including m sub-rotations 162 where no scanning is performed for all sub-rotations except a jth sub-rotation 164 in which a scan is performed. FIG. 5 illustrates an embodiment where n equals m, and where i equals j. FIG. 5 illustrates a fixed non-distributed ¼ scan because j and I sub-rotations 154 and 164 are 90°.

Figure 6:
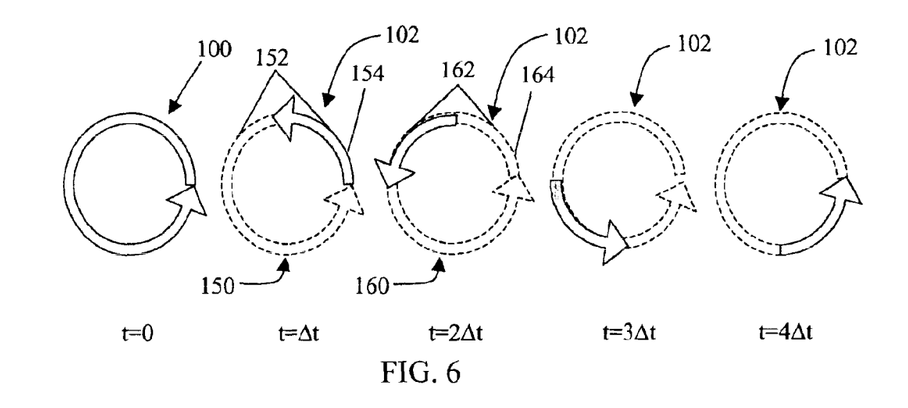
FIG. 6 illustrates a rotating partial scan.

FIG. 6 shows a further embodiment of FIG. 4 where n equals m, and where i is not equal to j. FIG. 6 illustrates a non-fixed non-distributed ¼ scan because j and I sub-rotations are 90° and not fixed (i.e., rotated).

Figure 7:
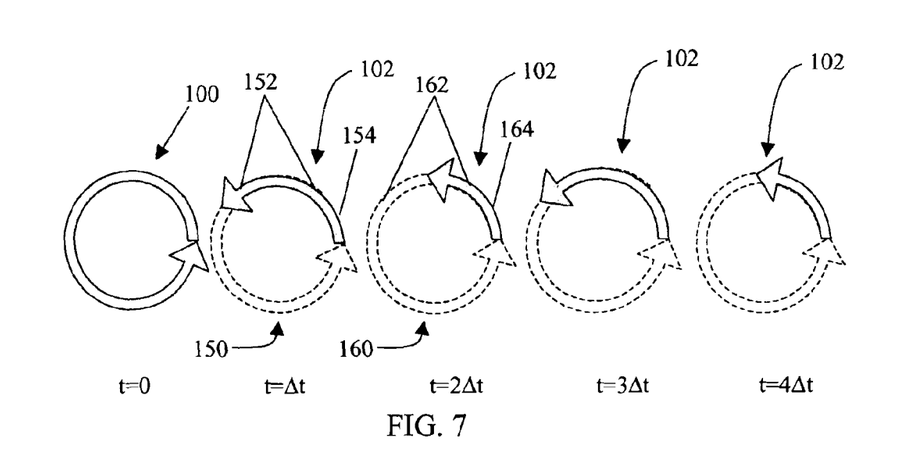
FIG. 7 illustrates a fixed partial scan.

FIG. 7 shows a further embodiment of FIG. 4 where n is not equal to m and where i equals j.

Figure 8:
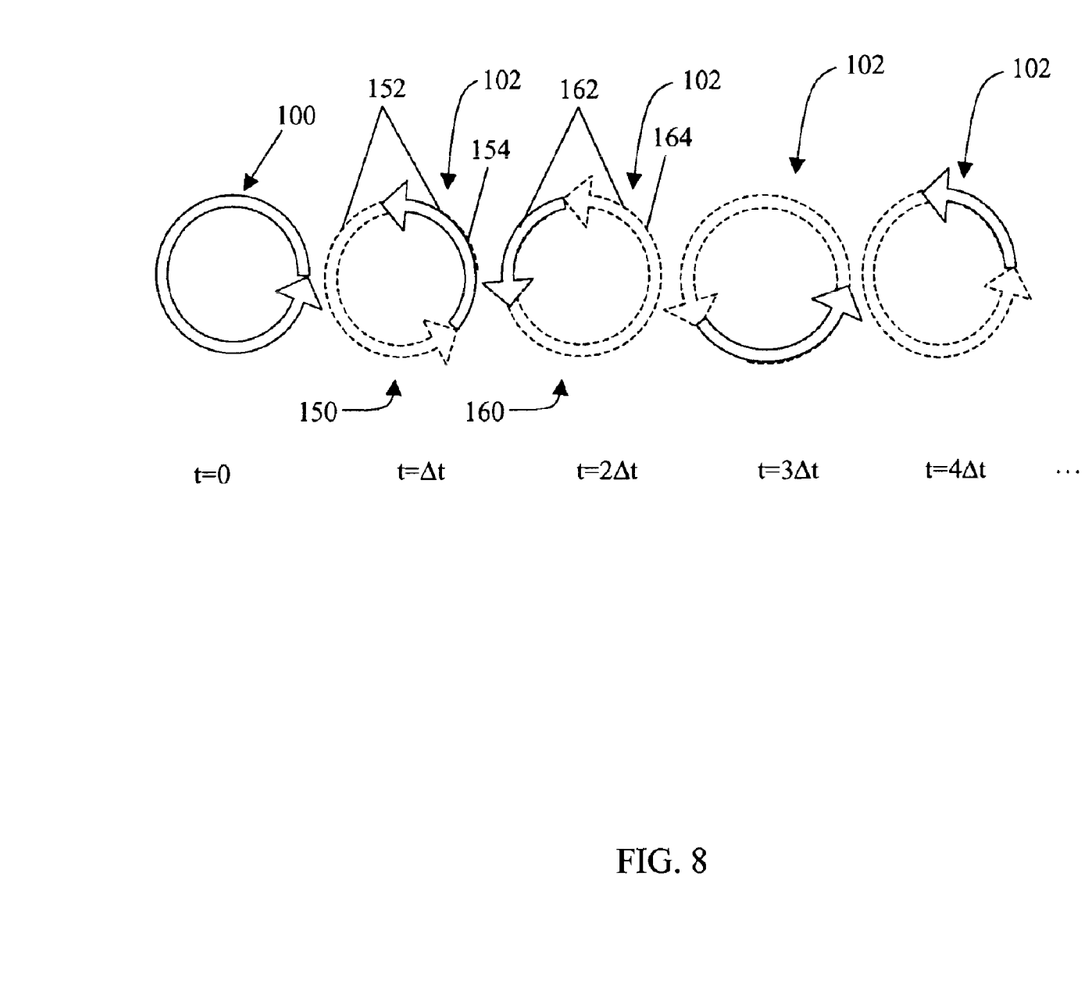
FIG. 8 illustrates a rotating partial scan.

FIG. 8 shows a further embodiment of FIG. 4 where n is not equal to m and where i is not equal to j.

In performing a sequence of partial scans, m may not be equal to n. Two examples are shown in FIGS. 7 and 8. These figures illustrate using alternating angular span sizes, one being greater than the other, to improve the accuracy of the estimate for constructing an image. Another example is, after the initial full scan and subsequent partial scans, periodically performing another full scan. This additional full scan further ensures the accuracy by periodically taking a complete dataset as a new base line. The tradeoff of these examples are between radiation dose and image quality.

The embodiments of FIG. 4 through FIG. 8 illustrate 90° and 120° data collection. These sub-rotation angular spans are not intended to be interpreted as excluding the use of other sub-rotation angular spans. The angular span set to 120° facilitates improving the accuracy of the image estimation over 90°. In this though, the amount of dose reduction is compromised. Therefore, in another embodiment, the angular span is set to 80°, using three segments and a half-scan algorithm for image reconstruction.

Figure 9:
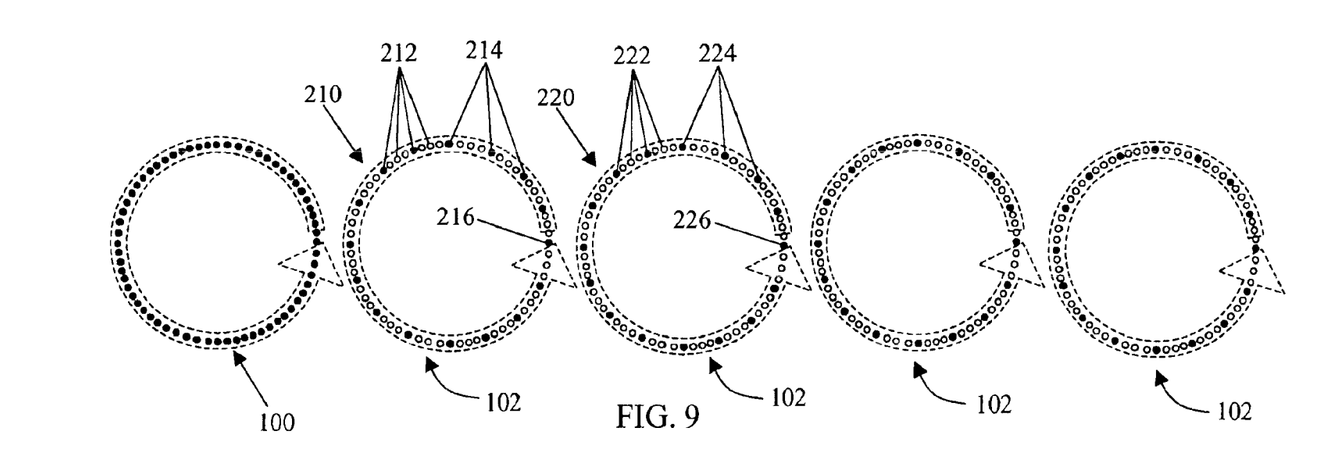
FIG. 9 illustrates a fixed distributed scan.

FIG. 9 illustrates partial scans 102 of another embodiment of FIG. 4, including performing a first full rotation 210 including n view-indexes 212, where no scanning is performed for all view-indexes except every ith view-index 214 beginning with a view-index q 216 in which a scan is performed. This is followed by performing a second full rotation 220 including m view-indexes 222 where no scanning is performed for all view-indexes except every jth view-index 224 beginning with a view-index r 226 in which a scan is performed. FIG. 9 illustrates an embodiment where q equals r and n equals m. FIG. 9 illustrates a fixed distributed ¼ scan because the views where data is collected totals 90° and are distributed (i.e., not consecutive).

Figure 10:
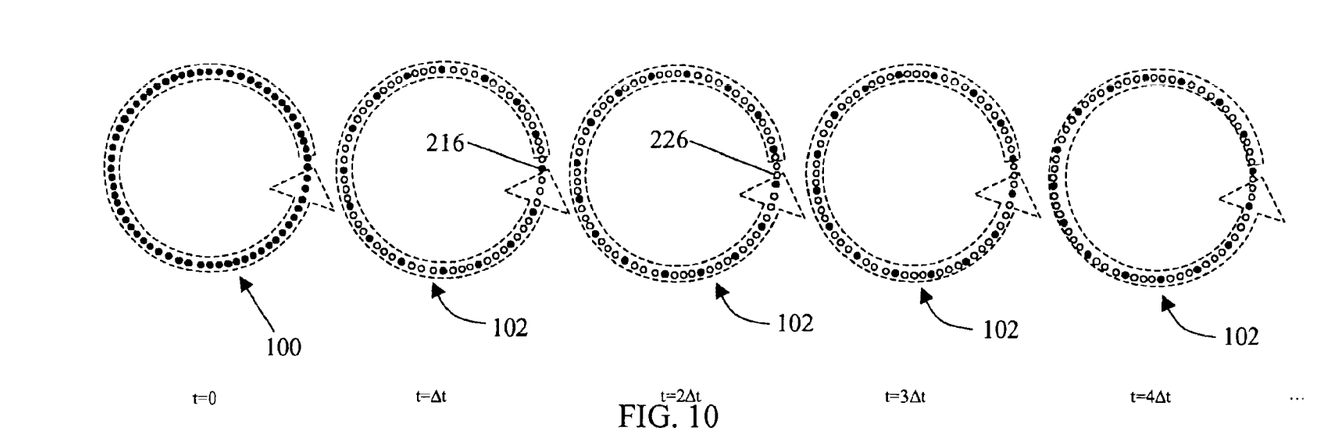
FIG. 10 illustrates a rotating distributed scan.

FIG. 10 shows a further embodiment of FIG. 9 where q is not equal to r. FIG. 10 illustrates a rotating distributed ¼ scan because the data collection views rotate in subsequent scans.

Performing scans of an object of interest utilizing the partial scan protocol results in projection datasets that are collected for constructing images. Following the partial scanning protocol, two methods of forming the images are interpolation and extrapolation of the collected projection datasets.

Figure 11:
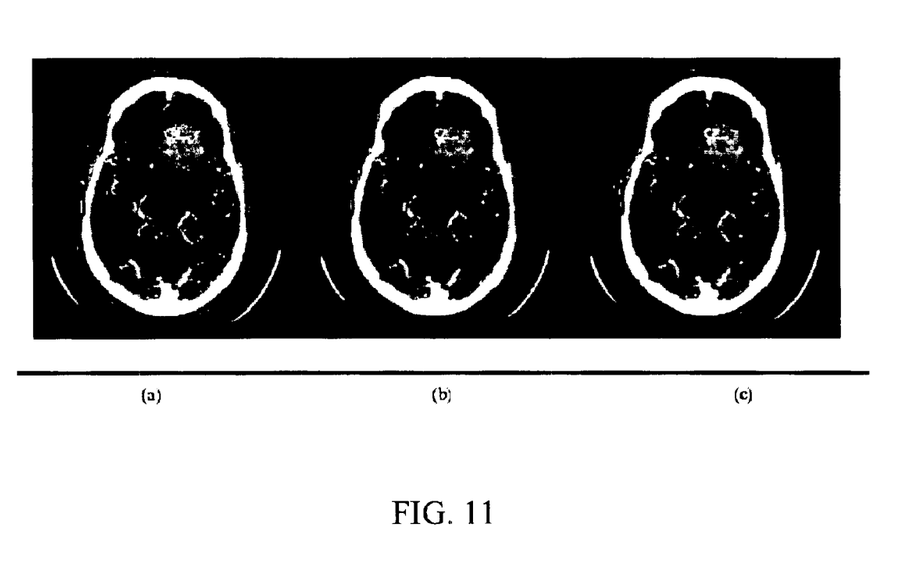
FIG. 11 shows head perfusion images.

FIG. 11 shows perfusion images reconstructed from performing interpolation calculations on the collected datasets. FIG. 11 shows reconstructed perfusion images with: (a) FBP based on full scan, (b) filtered back-projection (FBP) based on a 90° scan (shown in FIG. 6) and linear interpolation, and (c) Ordered Subset Expectation Maximization (OSEM) based on a 90° scan (shown in FIG. 6) and linear interpolation. All of the images correspond to 20 seconds after the initial data acquisition.

As an example, FIG. 6 shows a 90° scan protocol. For t=0, as the very first scan, 0°–360° projection data is collected. The projection is denoted by $p_0$(0–360). At t=$\Delta$t, 0°–90° projection is collected. Similarly, this projection is denoted by $p_{\Delta t}$(0–90). In the same fashion, projections at angles 90°–180°, 180°–270°, and 270°–360°, are collected t=2$\Delta$t, t=3$\Delta$t and t=4$\Delta$t, respectively. These projections are denoted by $p_{2\Delta t}$(90–180), $p_{3\Delta t}$(180–270), $p_{4\Delta t}$(270–360) respectively. This process continues until the entire perfusion data collection ends.

From t=$\Delta$t on, the other projections (i.e., views in which no data collection occurs) can be estimated by linear interpolation from the above collected projections. For the image corresponding to t=0, the reconstruction process is straightforward since the entire 360° data is available. For the image corresponding to t=$\Delta$t, a set of projections P'$_{\Delta t}$ (90–360) are first estimated as follows $$p'_{\Delta t}(90-180) = \frac{p_0(90-180) + p_{2\Delta t}(90-180)}{2}, \quad (1)$$

$$p'_{\Delta t}(180-270) = \frac{2p_0(180-270) + p_{3\Delta t}(180-270)}{3},$$

$$p'_{\Delta t}(270-360) = \frac{3p_0(270-360) + p_{4\Delta t}(270-360)}{4}.$$

Similarly, projections corresponding to t=2$\Delta$t, t=3$\Delta$t, etc. are estimated by linear interpolation. Note that on estimation of a projection dataset, a measured dataset is used, that is closest temporally to the time instant of interest.

Based on the estimated projection dataset, either filtered back-projection technique (FBP) or iterative reconstruction technique or another desirable technique is used to perform the image reconstruction. The FBP approach has an advantage of computational simplicity. On the other hand, an iterative algorithm has an advantage of further reducing any noise in the reconstructed images.

Note that for t=0, the very first scan, data is collected for a full scan, 0–360° projection. As noted above, at any scan time, another full-scan can be performed to further ensure the accuracy by taking a complete dataset periodically as a new base line. Also, the linear interpolation can be replaced by other interpolation, such as a higher order interpolation.

One characteristic of the Partial Scan Protocol (PSP) and the Projection Interpolation Algorithm (PIA) is to collect a part of projections needed for a time instant of interest, estimate missing projections by means of interpolation from their neighboring projections, and reconstruct an image subsequently. As compared to the known method illustrated in FIG. 3, one advantage of the method illustrated in FIG. 4 is that the projection data collected has a sufficient signal-to-noise ratio, therefore it is unnecessary to reduce noise in either projection or image domains, or if noise reduction is performed, the amount of noise reduction is less using the method illustrated in FIG. 4 than the method illustrated in FIG. 3.

In the Projection Interpolation Algorithm (PIA), the interpolation can result in some error in projection data. Alternatively, the Partial Scan Protocol (PSP) and an Image Prediction Algorithm (IPA) can be used. This method works on collected projections only so interpolation error is avoided.

Partial projections are collected as before, and the image is reconstructed from the collected data by OSEM (Ordered Subset Expectation Maximization) with the predictive image as the "initial guess". Note that in head perfusion, the image becomes bright and then dark gradually as the contrast medium circulates in the body. This regularity makes it possible to predict the current image by extrapolation from the images reconstructed earlier.

Figure 12:
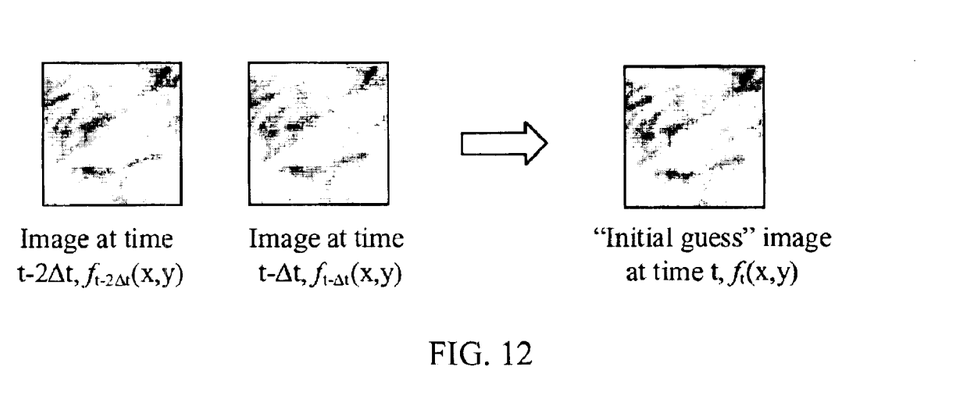
FIG. 12 shows image space prediction for the initial image to be used in iterative reconstruction.

In order to describe the prediction process clearly, linear extrapolation is used as an example. FIG. 12 illustrates two images used to reconstruct an image by OSEM, the "initial guess" being estimated based on the two images generated at the two previous adjacent time intervals.

Let us denote the "initial guess" image for OSEM reconstruction at time t by $f_t(x, y)$, the two adjacent images generated at t-$\Delta$t and t-2$\Delta$t respectively by $f_{t-\Delta t}(x, y)$ and $f_{t-2\Delta t}(x, y)$. The linear prediction can be carried out in the following manner:

$$f_t(x, y) = 2f_{t-\Delta t}(x, y) - f_{t-2\Delta t}(x, y). \quad (2)$$

In this algorithm, the Partial Scan Protocol (PSP) is less restrictive than that for the Projection Interpolation Algorithm (PIA) because the unknown projections are not estimated from the collected projection. Hence, there are more alternative scanning protocols available for choice. As an example of the FIG. 9 embodiment, using fixed distributed ¼ scan protocol, for t=0 a complete 360° projection dataset is collected, but for t=Δt and other later instants only the projection data with view indexes 0, 4, 8, . . . (the black circles) are collected. In the rotating distributed ¼ scan (as shown in FIG. 10), for t=Δt only the projection data with view indexes 0, 4, 8, . . . are collected, but for t=2Δt only the projection data with view indexes 1, 5, 9, . . . are collected, and so on.

Figure 13:
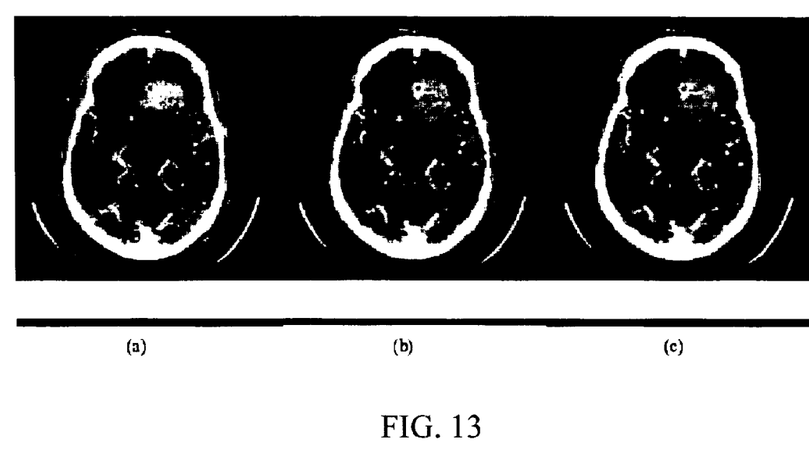
FIG. 13 shows images reconstructed via linear image prediction.

FIG. 13 shows images reconstructed via linear image prediction, using three scan protocols (a) fixed 90° scan (shown in FIG. 4), (b) fixed distributed ¼ scan (shown in FIG. 9), and (c) rotating distributed ¼ scan (shown in FIG. 10). The first image (t=0) is reconstructed from a 360° projection dataset. This image is used as an "initial guess" for reconstruction of the second image (t=Δt). From the third image on, the linear extrapolated image according to (2) is used as the initial image. The reconstructed images in FIG. 13 correspond to the time instant 20 seconds after the initial data acquisition.

Note that the linearly extrapolation method serves as an illustrative example. Other prediction methods can also be used. For example, higher-order extrapolation methods may be used. Generally, one characteristic of the Partial Scan Protocol (PSP) and the Image Prediction Algorithm (IPA) is that only a part of projections is really collected, and the OSEM or another suitable method can be applied just to these collected projections. Since the images change very slowly during head perfusion, one can predict the next image precisely as an excellent initial guess. In this case, the OSEM works effectively to suppress small differences between the measured data and the synthesized data based on an intermediate reconstructed image. Technical effects of the herein described methods and apparatus include low noise images and reduced dosage.

While the invention has been described in terms of various specific embodiments, those skilled in the art will recognize that the invention can be practiced with modification within the spirit and scope of the claims.

What is claimed is:

1. A method for conducting a perfusion study, said method comprising:
    performing an initial full computed tomography scan of an area of interest in an object; and
    performing at least one subsequent partial computed tomography scan of the area of interest to detect motion of a contrast agent.

2. A method in accordance with claim 1 wherein said performing at least one subsequent partial scan comprises:
    performing a first full rotation including n sub-rotations, where no scanning is performed for all sub-rotations except an ith sub-rotation in which a scan is performed; and
    performing a second full rotation including m sub-rotations where no scanning is performed for all sub-rotations except a jth sub-rotation in which a scan is performed.

3. A method in accordance with claim 2 wherein said performing a second full rotation comprises performing a second full rotation including m sub-rotations where no scanning is performed for all sub-rotations except a jth sub-rotation in which a scan is performed wherein m=n, and j=i.

4. A method in accordance with claim 2 wherein said performing a second full rotation comprises performing a second full rotation including m sub-rotations where no scanning is performed for all sub-rotations except a jth sub-rotation in which a scan is performed wherein m=n, and j≠i.

5. A method in accordance with claim 2 wherein said performing a second full rotation comprises performing a second full rotation including m sub-rotations where no scanning is performed for all sub-rotations except a jth sub-rotation in which a scan is performed wherein m≠n, and j=i.

6. A method in accordance with claim 2 wherein said performing a second full rotation comprises performing a second full rotation including m sub-rotations where no scanning is performed for all sub-rotations except a jth sub-rotation in which a scan is performed wherein m≠n, and j≠i.

7. A method in accordance with claim 2 further comprising:
    collecting projection data from the partial scans;
    forming a partial projection dataset from the collected projection data;
    interpolating the partial projection data to estimate a complete projection dataset from the partial dataset; and
    reconstructing images from the estimated complete projection dataset.

8. A method in accordance with claim 1 wherein said performing at least one subsequent partial scan comprises:
    performing a first full rotation including n view-indexes, where no scanning is performed for all view-indexes except every ith view-index beginning with a view-index q in which a scan is performed; and
    performing a second full rotation including m view-indexes where no scanning is performed for all view-indexes except every jth view-index beginning with a view-index r in which a scan is performed.

9. A method in accordance with claim 8 wherein said performing a second full rotation comprises performing a second full rotation including m view-indexes where no scanning is performed for all view-indexes except every ith view-index beginning with a view-index r in which a scan is performed, wherein r=q.

10. A method in accordance with claim 8 wherein said performing a second full rotation comprises performing a second full rotation including m view-indexes where no scanning is performed for all view-indexes except every jth view-index beginning with a view-index r in which a scan is performed, wherein r≠q.

11. A method in accordance with claim 8 further comprising:
    collecting projection data from the partial scans;
    reconstructing at least two images from the collected projection data;
    extrapolating an initial guess image based on the at least two images; and
    constructing subsequent images based on the extrapolated initial guess image.

12. A Computed Tomography (CT) System comprising:
    an x-ray radiation source;
    an x-ray radiation detector; and
    a computer coupled to said radiation source and said radiation detector, said computer configured to:
        perform an initial full computed tomography scan of an area of interest in an object; and perform at least one subsequent partial computed tomography scan of the area of interest to detect motion of a contrast agent.

13. A system in accordance with claim 12, wherein said computer further configured to:

perform a first full rotation including n sub-rotations, where no scanning is performed for all sub-rotations except an ith sub-rotation in which a scan is performed; and perform a second full rotation including m sub-rotations where no scanning is performed for all sub-rotations except a jth sub-rotation in which a scan is performed.

14. A system in accordance with claim 13 wherein m=n and j=i.

15. A system in accordance with claim 13 wherein m=n and j≠i.

16. A system in accordance with claim 13 wherein m≠n and j=i.

17. A system in accordance with claim 13 wherein m≠n and j≠i.

18. A system in accordance with claim 12, wherein said computer configured to perform at least one subsequent partial scan comprises a computer configured to:

perform a first full rotation including n view-indexes, where no scanning is performed for all view-indexes except every ith view-index beginning with a view-index q in which a scan is performed; and perform a second full rotation including m view-indexes where no scanning is performed for all view-indexes except every jth view-index beginning with a view-index r in which a scan is performed.

19. A system in accordance with claim 18 wherein r=q.

20. A system in accordance with claim 18 wherein r≠q.

21. A computer readable medium encoded with a program configured to:

perform an initial full computed tomography scan of an area of interest in an object; and perform at least one subsequent partial computed tomography scan of the area of interest to detect motion of a contrast agent.

22. A computer readable medium in accordance with claim 21 wherein said program further configured to instruct the computer to:

perform a first full rotation including n sub-rotations, where no scanning is performed for all sub-rotations except an ith sub-rotation in which a scan is performed; and perform a second full rotation including in sub-rotations where no scanning is performed for all sub-rotations except a jth sub-rotation in which a scan is performed.

23. A computer readable medium in accordance with claim 21 wherein said program further configured to instruct the computer to:

perform a first full rotation including n view-indexes, where no scanning is performed for all view-indexes except every ith view-index beginning with a view-index q in which a scan is performed; and perform a second full rotation including m view-indexes where no scanning is performed for all view-indexes except every ith view-index beginning with a view-index r in which a scan is performed.

* * * * *

UNITED STATES PATENT AND TRADEMARK OFFICE
CERTIFICATE OF CORRECTION

PATENT NO. : 6,934,353 B2 Page 1 of 1
APPLICATION NO. : 10/676215
DATED : August 23, 2005
INVENTOR(S) : Wang et al.

It is certified that error appears in the above-identified patent and that said Letters Patent is hereby corrected as shown below:

In Claim 9, column 8, line 42, delete "every ith" and insert therefor -- every jth --.
In Claim 22, column 10, line 16, delete "including in" and insert therefor -- incuding m --.
In Claim 23, column 10, line 28, delete "every ith" and insert therefor -- every jth --.

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

PATENT NO.         : 6,934,353 B2                                                               Page 1 of 1
APPLICATION NO. : 10/676215
DATED              : August 23, 2005
INVENTOR(S)        : Wang et al.

It is certified that error appears in the above-identified patent and that said Letters Patent is hereby corrected as shown below:

Title page item [73] should read:

GE Medical Systems Global Technology Company, LLC, Waukesha, Wisconsin (USA) and University of Iowa Research Foundation, Iowa City, Iowa (USA).

Signed and Sealed this

Twelfth Day of January, 2010

David J. Kappos
*Director of the United States Patent and Trademark Office*